Figure 1A:
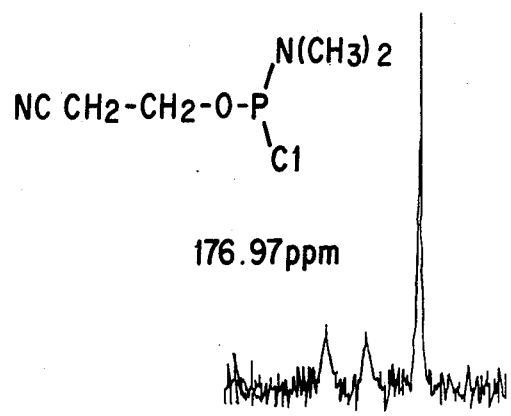

United States Patent [19]

Köster et al.

[11] Patent Number: 4,725,677

[45] Date of Patent: Feb. 16, 1988

[54] PROCESS FOR THE PREPARATION OF OLIGONUCLEOTIDES

[75] Inventors: Hubert Köster, Hamburg, Fed. Rep. of Germany; Nanda D. Sinha, Bundu Dt. Ranchi, India

[73] Assignee: Biosyntech GmbH, Fed. Rep. of Germany

[21] Appl. No.: 752,178

[22] PCT Filed: Aug. 10, 1984

[86] PCT No.: PCT/EP84/00244

§ 371 Date: Jun. 18, 1985

§ 102(e) Date: Jun. 18, 1985

[87] PCT Pub. No.: WO85/00816

PCT Pub. Date: Feb. 28, 1985

[30] Foreign Application Priority Data

Aug. 18, 1983 [DE] Fed. Rep. of Germany ....... 3329892

[51] Int. Cl.$^4$ ...................... C07H 15/12; C07H 17/00
[52] U.S. Cl. ......................................... 536/27; 536/28; 536/29
[58] Field of Search .............................. 536/27, 28, 29

[56] References Cited

U.S. PATENT DOCUMENTS

| | | | |
|---|---|---|---|
| 4,310,662 | 1/1982 | Crea | 536/27 |
| 4,415,732 | 11/1983 | Caruthers et al. | 536/27 |
| 4,419,509 | 12/1983 | Hsiung | 536/27 |
| 4,458,066 | 7/1984 | Caruthers et al. | 536/27 |
| 4,476,301 | 10/1984 | Imbach et al. | 536/29 |
| 4,500,707 | 2/1985 | Caruthers et al. | 536/29 |
| 4,591,614 | 5/1986 | Miller et al. | 536/27 |
| 4,605,735 | 8/1986 | Miyoshi et al. | 536/27 |

FOREIGN PATENT DOCUMENTS

| | | |
|---|---|---|
| 0040099 | 11/1981 | European Pat. Off. ............. 536/27 |
| 81302110.2 | 11/1981 | European Pat. Off. . |
| 82200564.1 | 11/1982 | European Pat. Off. . |
| 83870031.8 | 10/1983 | European Pat. Off. . |
| 84200951.6 | 1/1985 | European Pat. Off. . |

OTHER PUBLICATIONS

Lelsinger et al., "Jour. of the Amer. Chem. Soc." vol. 98, No. 12, Jun. 1976, pp. 3655–3661.
Narang, "Tetrahedron", vol. 39, No. 1. pp. 3–22, 1983.
Marugg et al., "Recl. Trav. Chim. Pays-Bas" vol. 103, pp. 97–98, 1984.
Clesen et al., "Tetrahedron Letters", vol. 25, No. 12, pp. 1307–1310, 1984.
Ogilvie, K. K. et al., Can J. Chem 58:2686 (1980).
V. Amarnath and A. D. Broom, Chemical Reviews 77(2)183 (1977).
H. Koster et al., Nucleic Acids Research Symposium Series No. 7 (1980) pp. 39–61.
Caruthers, M. H., Science 230:281 (1985).
Zon, G. et al. Nucleic Acids Research 13(22):8181 (1985).
Urdea, M. S. et al. Nucleic Acids Research Symposium Ser. 16 (1985) pp. 257–260.
Gao, X. et al. Nucleic Acids Research 13(2):573 (1985).
Beaucage and Caruthers (1981) Tet. Lett. 22:1859–1862.

Primary Examiner—Ronald W. Griffin
Attorney, Agent, or Firm—Hamilton, Brook, Smith and Reynolds

[57] ABSTRACT

The invention relates to a process for the preparation of oligonucleotides by the following steps: reaction of a nucleoside with a phosphine derivative, reaction of the nucleotide derivative thus obtained with a nucleoside bonded to a polymeric carrier, oxidation of the carrier-bound nucleoside-nucleotide thus obtained with formation of phosphotriester groups, blocking of free primary 5'-OH groups, elimination of a protective group from the terminal 5'-OH group, where appropriate single or multiple repetition of the abovementioned steps to introduce further nucleoside phosphate or oligonucleoside phosphate units, and cleavage of the nucleoside-carrier bond and, where appropriate, elimination of all protective groups present in the oligonucleoside phosphates. The phosphine derivative used is a compound of the general formula III

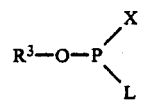

(III)

in which X and L can react with OH groups of the sugar units in the oligonucleotides, and $R^3$ is a protective group which can be liberated by $\beta$-elimination.

19 Claims, 12 Drawing Figures

FIG. 4

FIG. 5

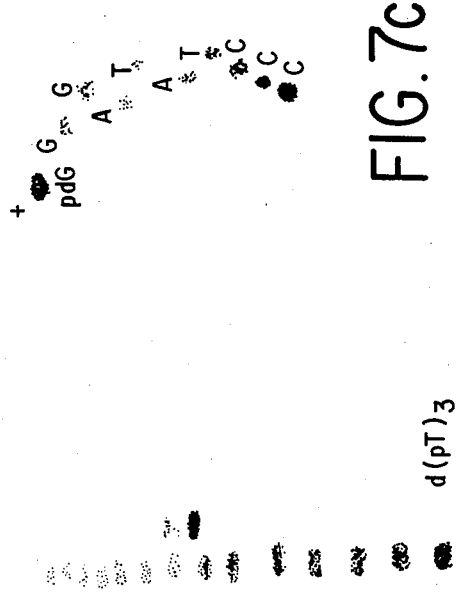
FIG. 7c
FIG. 7b
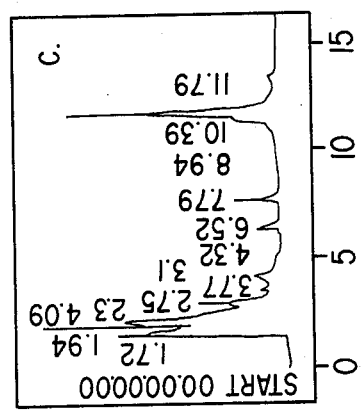
FIG. 7a

PROCESS FOR THE PREPARATION OF OLIGONUCLEOTIDES

DESCRIPTION

The invention relates to a process for the preparation of oligonucleotides of the general formula I indicated in claim 1. The oligonucleotides prepared according to the invention have defined sequences and can be used as specific primers and probes and are of great importance for the synthesis of complete genes (Arzneimittelforschung 30, 3a, 548, (1980)).

According to the most recent state of the art, oligonucleotides are prepared by either the phosphate or phosphite triester method using polymeric carriers (Nachr. Chem. Tech. Lab. 29, 230 (1981)). In order to be able to construct defined sequences, it is necessary for the individual units (nucleosides or nucleotides) to be provided with suitable protective groups. In this context, base-labile acyl groups are generally used for the protection of the exocyclic amino groups on the heterocyclic nucleobases, and a base-labile ester bond is used to attach the oligonucleotide chain to the polymeric carrier in a customary manner, and acid-labile trityl ether groups are used to protect the primary 5'-OH group. The phosphate protective group used in the phosphate triester method is customarily either the 2-chlorophenyl or the 4-chlorophenyl group, with an ester-type bond, which can only be removed by attack of a base or a nucleophile on the phosphorus atom. This type of step is inherently undesirable since it involves the risk of cleavage of the internucleotide phosphate ester bond. This risk has been greatly reduced by the use of oximate anions (Tetrahedron Lett. 19, 2727 (1978)), although these also attack the phosphorus atom in an undesired manner in the crucial step and, moreover, have the disadvantage that a relatively small amount of desired oligonucleotide is contaminated with every large amounts of involatile salts which are difficult to extract. This not only makes the working up and subsequent purification of the synthesized oligonucleotide difficult but also leads to considerable material losses.

In the phosphite triester method, the methyl group with an ester-type bond is customarily used as the phosphate protective group which can be removed by attack of a nucleophile on the methyl C atom (J. Amer. Chem. Soc. 99, 3526 (1977)). Since attack on the P atom is avoided, there is likewise avoidance of the risk of cleavage of the internucleotide bond. The nucleophile customarily used is thiophenol/triethylamine, which are unpleasant to manipulate and, moreover, lead to involatile compounds which are difficult to extract and which, as mentioned above, both make work-up difficult and lead to considerable material losses.

Although the actual synthesis of oligonucleotides by the solid phase/phosphite or phosphate triester method takes place very efficiently and rapidly, the preparation of oligonucleotides of defined sequence remains very time-consuming. This is primarily due to the problems of the subsequent work-up and purification which take up a multiple of the actual synthesis time. The process of the invention operates at this point and provides in this connection a crucial technical improvement.

In order to obtain compounds of the formula I indicated in claim 1,

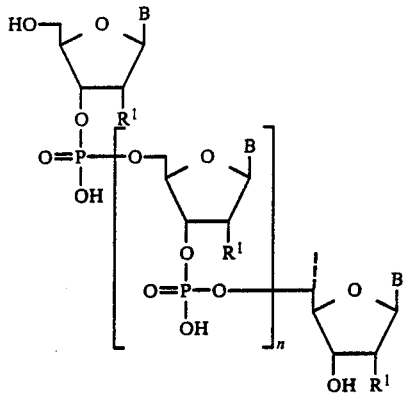

in which B denotes a nucleobase, for example adenine (A), guanine (G), cytosine (C), thymine (T) or uracil (U) or their analogs, and $R^1$ denotes hydrogen, hydroxyl or hydroxyl which is protected by the protective groups customary in nucleotide chemistry, and n denotes an integer from 1 to 200, according to the invention a variety of defined reaction steps are carried out, as follows:

(a) Reaction of a nucleoside of the general formula II.

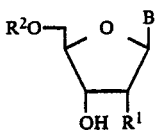

$R^1$ of the general formula II can be hydrogen; in this case the compounds of the formula I are oligodeoxynucleotides. The group $R^1$ can also be hydroxyl or hydroxyl which is, where appropriate, protected by the protective groups customary in nucleotide chemistry. Examples of protective groups of this type are trityl, monomethoxytrityl and dimethoxytrityl, acyl, for example acetyl, benzoyl; tetrahydropyranyl, methoxytetrahydropyranyl, o-nitrobenzyl and silyl ethers, such as, for example, t-butyldiphenylsilyl ethers. A general review of the protective groups customary in nucleotide chemistry is to be found in, for example, Tetrahedron 1981, pages 363–369, Liebigs Ann. Chem. 1978, 839–850, and Nucleic Acids Research, Symposium Series No. 7, 1980, 39–59.

$R^2$ is likewise a protective group customary in nucleotide chemistry according to the abovementioned publications, preferably the acid-labile 4,4'-dimethoxytrityl or 4,4',4''-trimethoxytrityl group. B' can likewise have a protective group customary in nucleotide chemistry according to the abovementioned prior publications.

The nucleoside of the formula II is reacted according to the invention with a phosphine derivative of the general formula III according to claim 1.

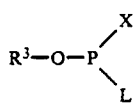

In the general formula, X denotes chlorine, bromine, CN or SCN; L denotes chlorine, bromine, CN, SCN or an amino radical of the formula —$NR_2^4$ (formula VIII), where the groups $R^4$ denote primary, or secondary or tertiary alkyl radicals having 1–10 carbon atoms, or together denote a cycloalkyl radical having 5–7 carbon atoms, optionally with alkyl branches, and/or can contain one or two nitrogen, oxygen and/or sulfur atoms as heteroatoms. The group L can also form a reactive heterocyclic radical, the imidazolyl, triazolyl, tetrazolyl, 3-nitro-1,2,4-triazolyl, thiazolyl, pyrrolyl, benzotriazolyl (optionally with substituents in the phenyl moiety) or benzohydroxytriazolyl (optionally with substituents in the phenyl ring) and the like.

$R^3$ in the phosphine derivative of the general formula (III) is, according to the invention, a group of the general formula VII,

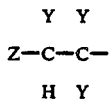

which can be removed with the aid of bases by β-elimination and in which Y denotes hydrogen, methyl or ethyl. Z represents an electron-attracting group, for example, halogen, such as fluorine, chlorine or bromine, CN or $NO_2$. Z can also denote phenyl, phenylthio, phenylsulfoxy or phenylsulfonyl, it being possible for the phenyl radicals to be substituted in the o, o'-position and/or p-position with halogen, CN or $NO_2$. It is also possible for one of the groups $CF_3$, $CCl_3$ or $CBr_3$ to replace the group

The reaction according to step a takes place in the presence of an organic base.

(b) Reaction of the nucleoside-phosphorous acid derivative, of the formula IV, obtained in step a.

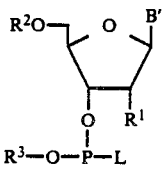

The reaction of the compound according to formula IV is carried out with a nucleoside of the general formula V according to claim 1, which is bound to a polymeric carrier.

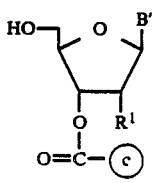

It is possible to use soluble or insoluble, that is to say crosslinked, polymeric carriers, for example modified silica gel, glass, especially "controlled pore glass", polyester, polyamide, polyvinyl alcohol, polysiloxane, polystyrene or the like. Ester bonds are suitable and preferred for the attachment between the carrier and the nucleoside, including those derived from the levulinyl or β-benzoylpropionyl radical; the latter ester bonds can be cleaved with hydrazine under neutral conditions. The acid-labile trityl ether bond, optionally with substituents in the phenyl rings, is also suitable as a method of attachment, compare Liebigs Ann. Chem. 1974, 959.

(c) Oxidation of the carrier-bond nucleotide-nucleoside, of the general formula VI, obtained in step b.

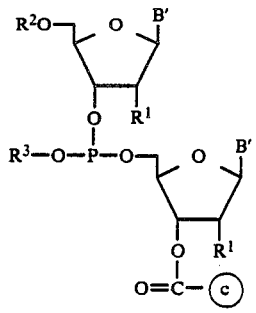

Oxidation leads to a phosphate group; this can be carried out with, for example, iodine/$H_2O$, $H_2O_2$ or organic peracids or, in general, by oxidation by introduction of O, S or Se.

(d) Blocking of free primary 5'-OH groups which have not been reacted in the reaction according to step b (in the product of the formula V).

These free hydroxyl groups are blocked with a permanent protective group, for example by reaction with acetic anhydride.

(e) Elimination of the protective group(s) $R^2$.

The elimination is carried out using, for example, a protonic acid or Lewis acid, such as $ZnBr_2$ or dialkylaluminum chloride, when $R^2$ represents a trityl group or a methoxy derivative thereof.

(f) Introduction of further nucleoside phosphate or oligonucleoside phosphate units.

Steps a–e can be repeated to introduce at least one nucleoside phosphate moiety. Of course, when oligonucleoside phosphate units are employed, the chains are lengthened by more than one nucleoside phosphate unit.

(g) Elimination of all protective groups.

This elimination can be carried out in such a manner that, using aqueous ammonia, in one step the N-acyl groups on the heterocyclic bases, the ester bond between the oligonucleotide and the carrier (the latter can, where appropriate, also be cleaved with hydrazine under neutral conditions) and the phosphate protective group are eliminated by β-elimination in accordance with the general scheme 1 at the end of the description. An oligonucleotide having only a 5'-terminal trityl protective group is then obtained, and this can be purified directly in a manner known per se, after removal of the volatile base (ammonia), by high-pressure liquid chromatography (HPLC) on reverse phase material.

The intermediates of the general formula IV according to claim 1 are new compounds. They are in the form of very stable compounds which can be prepared in the pure form and are easy to manipulate but nevertheless are very reactive in the sense of forming internucleotide bonds. The use of $R^3$ as a protective group which can be removed by bases via β-elimination makes is possible for the first time to eliminate all the protective groups, apart from the 5'-trityl group, in one step where, in an advantageous manner, by the use of volatile bases the desired oligonucleotide is contaminated with foreign materials to only a very small extent and thus directly afterwards can be purified by reverse phase HPLC due to the hydrophobic 5'-trityl group which is still present.

A further advantage of the process of the invention results from the fact that, due to the removal of the protective group by β-elimination, no attack on the P-atom takes place and thus none of the newly formed internucleotide bonds can be cleaved during the deprotection. Thus, the process of the invention takes very much less time and leads to overall purer products than do the processes hitherto available.

The invention is illustrated in detail below by means of examples, the phosphine derivatives used being those in which $R^3$ is a β-cyanoethyl group. Details of the reaction and physical characteristics of the compounds prepared can be seen in schemes 2 and 3, Table 1, and FIGS. 1-7 at the end of the description.

EXAMPLE 1

Preparation of phosphine derivatives of the general formula III:

β-Cyanoethyl phosphoramidochloridite:

A general summary of the reaction can be seen in scheme 2.

Apart from some improvements, dichloro- -cyanoethoxyphosphine (1) is prepared as in Can. J. Chem. 58, 2686 (1980):

300 ml of ether and 79.0 g (1 mol) of pyridine are added through a dropping funnel to 137.5 g (1.0 mol) of $PCl_3$ in a three-neck flask; the mixture is cooled to −78° C. under argon. Then a solution of 71.0 g (1 mol) of β-cyanoethanol in 150 ml of dry ether is added dropwise over the course of 1 to 1.5 hours. The cooling bath is removed; stirring is continued at room temperature for a further 3 hours (where necessary, another 300 ml of ether are added in order to ensure better stirrability). The stirrer and dropping funnel are removed under argon; the mixture is stored at 0° C. overnight. The solid salts are removed under argon; the precipitate is washed twice with 75 ml of ether each time. The combined organic phases are concentrated in vacuo; the residue is finally distilled in vacuo: boiling point 70°-75° C./0.4 mm Hg.

-Cyanoethyl phosphoramidochloridite (3):

A solution of 17.2 g (0.1 mol) of β-cyanoethyl phosphorodichloridite (1) in 60 ml of ether is added dropwise, over the course of 1 to 1.5 hours, to a solution of the N-trimethylsilylated secondary amine (0.1 mol) or secondary amine (0.2 mol) in 30 ml of ether at −20° C. under argon. After stirring at room temperature for 20 hours, the amine hydrochloride is removed; the remaining solution is concentrated. The residue is finally distilled in vacuo in a short-path distillation apparatus.

The physical properties of the compounds thus obtained are summarized in Table 1.

Figure 1B:
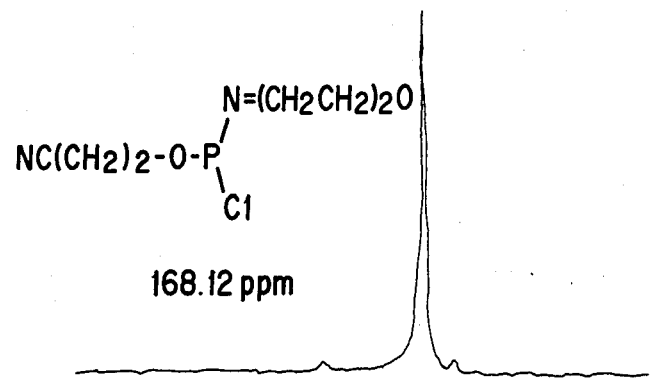

FIGS. 1a, 1b and 1c show $^{31}P$ NMR spectra of three different β-cyanoethyl phosphoramidochloridites.

The N-morpholine derivative is too unstable to heat for distillation to be possible. Nevertheless, the preparation is so pure that the residue can be used directly for the preparation of the activated nucleoside derivatives. The purity is usually greater than 95% according to the $^{31}P$ NMR spectra.

Nucleoside β-cyanoethyl phosphoramidites:

The preparation of the appropriately protected nucleoside β-cyanoethyl phosphoramidites can be seen in scheme 3.

The synthesis in analogy to Tetrahedron Lett. 22, 1859 (1981), with some improvements, provides good yields.

3.0 mmol of the N-protected 5'-dimethoxytritylated deoxynucleoside are dried azeotropically using THF/toluene, dissolved in 15 ml of dry THF, and 12.0 mmol of N,N,N-diisopropylethylamine are added. 6.0 mmol of the β-cyanoethyl phosphoramidochloridite are added dropwise to the solution under argon, with vigorous stirring, over the course of 2 minutes. After a short time (2 to 5 minutes), the amine hydrochloride precipitates out. The suspension is stirred for a further 30 to 40 minutes. The amine hydrochloride is filtered off under argon and thoroughly washed with dry THF (10 to 15 ml). The entire organic phase is concentrated and dissolved in argon-saturated ethyl acetate (100 ml). The organic phase is extracted twice with 50 ml each time of argon-saturated 10% aqueous sodium carbonate solution. The organic phases are dried with sodium sulfate and evaporated under reduced pressure to give a foam. The foam is dissolved in a little ethyl acetate or toluene and precipitated in n-hexane at −78° C. The activated nucleosides are stable for several months when stored at −20° C. under argon.

Figure 2:
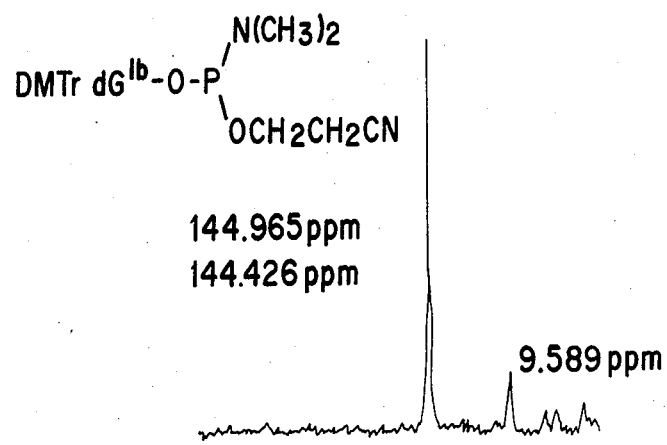

FIG. 2 shows the $^{31}P$ NMR spectrum of one of the activated deoxynucleosides.

Synthesis of d(CGGTACCG)

100 mg of "controlled pore glass" (CPG) loaded with a total of 8 umol of N-isobutyryldeoxyguanine (compare Tetrahedron Lett. 24, 747 (1983)) are consecutively condensed with the 5'-dimethoxytritylated N-acylated β-cyanoethyl N,N-diisopropylphosphoramidites of the deoxynucleosides C, C, A, T, G, G and C, in each case 20 to 25 equivalents of the phosphoramidite in acetonitrile being activated with 75-80 equivalents of sublimed tetrazole. The condensations are complete within 30 minutes at the most; the coupling yield is greater than 94%. After each condensation, oxidation with $I_2/H_2O$ and blocking of unreacted 5'-OH groups with acetic anhydride are carried out. Then the dimethoxytrityl group is eliminated either with 3% trichloroacetic acid in nitromethane/1% methanol or $ZnBr_2$/nitromethane/1% $H_2O$.

The overall yield of the protected octanucleotide at the end of all condensation steps is 55% based on carrier-bound deoxyguanosine.

Figure 3:
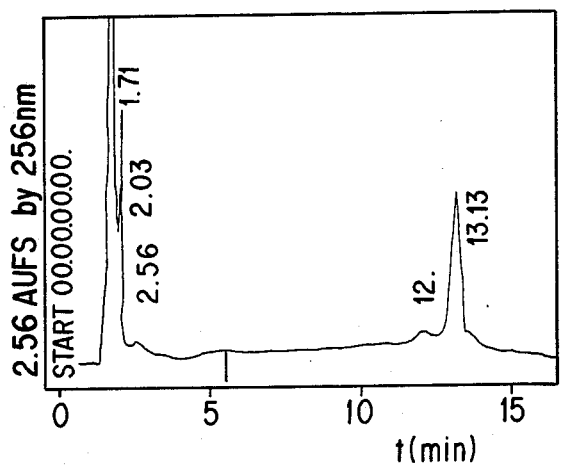

Complete deprotection and cleavage off from the carrier is achieved in one step by reaction of the glass beads with concentrated aqueous ammonia (3 ml) at 50° C. for 16 hours. The glass beads are then thoroughly washed with 50% aqueous methanol (3 times with 3 ml each time). The liquid phase is removed by evaporation (removal of the methanol) and freeze-drying. Then an aliquot is filtered through a millipore filter and purified by HPLC or RP 18 as can be seen in FIG. 3.

The fractions which contain the 5'-dimethoxytritylated oligonucleotide are collected; the volatile buffer is removed in a rotary evaporator in vacuo. 1 ml of 80% strength acetic acid is added to the residue. After 45 minutes at room temperature, the acetic acid is removed by freeze-drying.

Figures 4, 5:
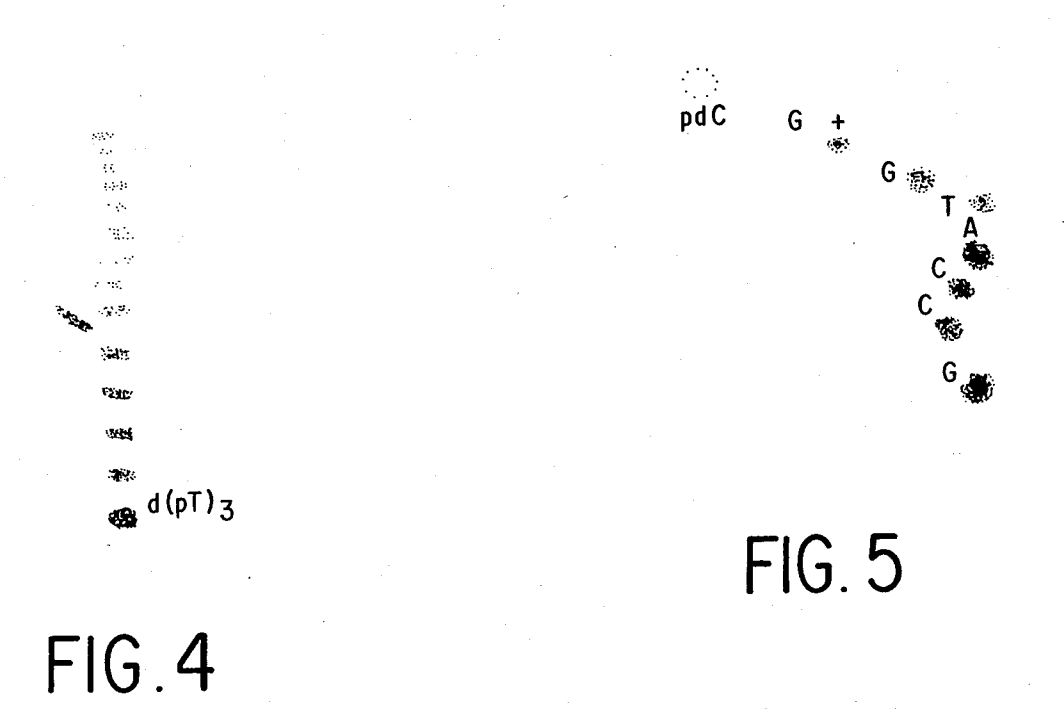

The material thus obtained is phosphorylated in the customary manner (Liebigs Ann. Chem. 1978, 982) with T4-polynucleotide kinase and γ-$^{32}$P-ATP. The resulting product is characterized by polyacrylamide gel electrophoresis comparing with a homo-oligo-dT chain length standard (Nucleic Acids Res. 6, 2096 (1979), FIG. 4)

and by sequencing according to FIG. 5 (Liebigs Ann. Chem. 1978, 982).

Figure 6C:
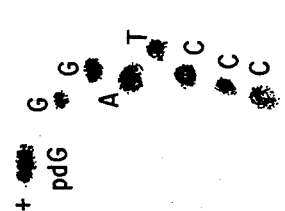
Figure 6B:
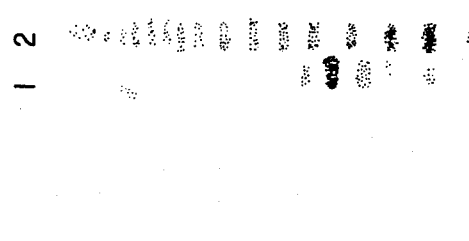
Figure 6A:
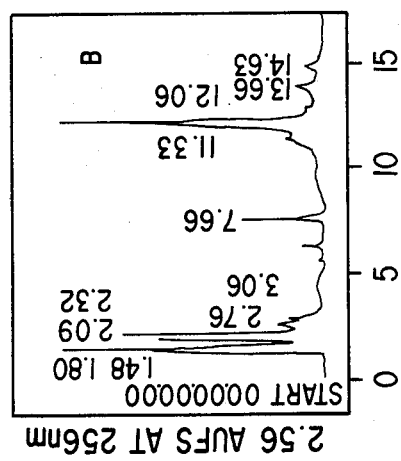

FIGS. 6a to 6c show the results (HPLC, gel electrophoresis, sequencing) of the synthesis of d(GGGATCCC) using the nucleoside β-cyanoethyl N,N-dimethylphosphoramidites. FIGS. 6a to 6c show the results (HPLC, g, electrophoresis, sequencing) of the synthesis of d(GGGATATCCC) using the nucleoside β-cyanoethyl N,N-morpholinophosphoramidites.

The results given in FIGS. 3, 6a and 7a were obtained by using a gradient from 10 to 25 vol. % CH₃CN, 5 min, and 25 to 29 vol. % CH₃CN, 30 min, in 0.1M triethylammonium acetate at pH 7.0.

TABLE 1

Physical data of β-cyanoethyl phosphoramidochlorites

| Compound | 3a<br>L = N,N—dimethylamino | 3b<br>L = N,N—diisopropylamino | 3c[1]<br>L = N—morpholino |
|---|---|---|---|
| Boiling point | 90–92°/0.6 mm | 103–5°/0.08 mm | — |
| Chemical shift[2] in ³¹P NMR in CH₃CN | 175.97 ppm | 179.82 ppm | 168.22 ppm |
| Chemical shift in ¹H NMR in ppm | 4.01, 4.17 (2t, P—OCH₂, 2H)<br>2.71 (t, —CH₂—CN, 2H)<br>2.7 (d, N(CH₃)₂, 6H) | 4.02, 4.2 (2t, POCH₂, 2H)<br>3.8 (m, N(CH)₂, 2H)<br>2.77 (t, —CH₂CH, 2H)<br>1.29 (d, N—CH(CH₃)₂, 12H) | 3.96, 4.1 (2t, POCH₂, 2H)<br>3.67 (t, O(CH₂)₂, 4H)<br>3.17 (m, P—N(CH₂)₂, 4H)<br>2.74 (t, CH₂—CN₂, 2H) |
| Mass spectrum | $\left(\frac{m}{e}\right)^+ = 180, 182 (+2), 145$<br>(—Cl), 136 (—C₂H₆N), 110 (—C₃H₄NO) | $\left(\frac{m}{e}\right)^+ = 236, 238 (+2), 201$<br>(—Cl), 166 (—C₃H₄NO), 136 (—C₆H₁₄N) | $\left(\frac{m}{e}\right)^+ = 222, 224 (+2), 187$<br>(—Cl), 152 (—C₃H₄NO), 136 (—C₄H₈O) |

[1]The crude product after removal of amine hydrochloride and compounds volatile under high vacuum at room temperature has a purity of 93–95% according to the ³¹P NMR spectrum
[2]The chemical shifts are determined in acetone-d₆ with 80% strength H₃PO₄ as the external standard.

Scheme 1.
Removal of the group R³ by β-elimination.

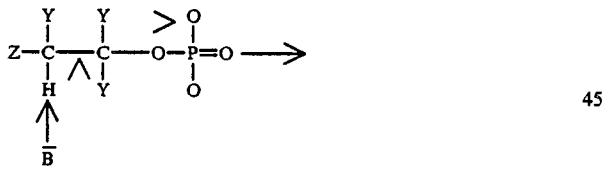

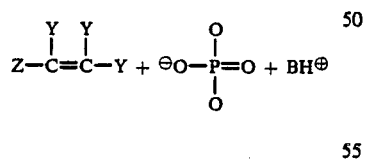

SCHEME 2

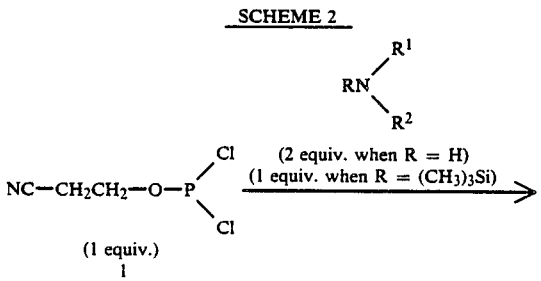

-continued
SCHEME 2

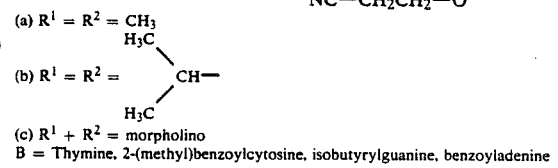

(a) $R^1 = R^2 = CH_3$
(b) $R^1 = R^2 = \begin{matrix} H_3C \\ H_3C \end{matrix} CH—$
(c) $R^1 + R^2 = $ morpholino
B = Thymine, 2-(methyl)benzoylcytosine, isobutyrylguanine, benzoyladenine

We claim:
1. A process for the preparation of oligonucleotides of the general formula I

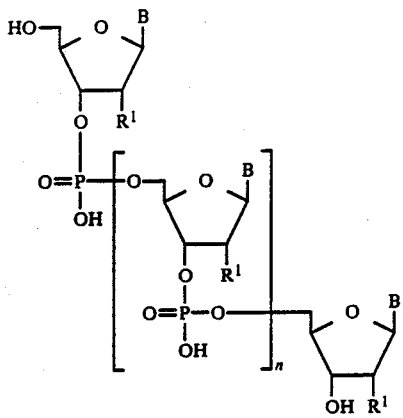 (I)

in which B denotes a nucleoside base, R¹ denotes hydrogen, hydroxyl or hydroxyl which is protected by a removable protective group and n denotes an integer from 1 to 200, comprising the steps of (a) reacting a nucleoside of the general formula II

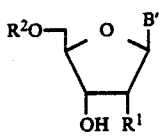 (II)

in which R¹ as defined as above, and R² denotes a removable protective group and B' denotes the nucleoside base B protected by the protective groups which can be eliminated, with a phosphine derivative of the general formula III

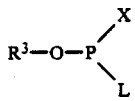 (III)

in which R³ is a protective group which can be eliminated, and X and L are groups which react with hydroxyl groups in the sugar moieties of the nucleotides or nucleosides, in the presence of a base to thereby form a nucleotide phosphite (b) reacting the nucleotide phosphite obtained in step (a) and represented by the formula IV:

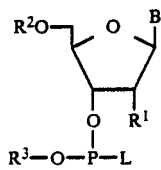 (IV)

in which B', R¹, R², R³ and L are as defined above, with a nucleoside, of the general formula V, bound to a polymeric carrier

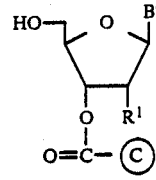 (V)

in which B' and R¹ are as defined above and C denotes the polymeric carrier;

(c) oxidizing the carrier-bound nucleoside-nucleotides obtained in step (b) and represented by the formula:

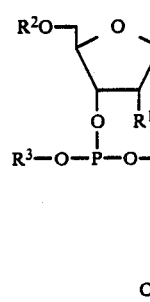 (VI)

in which B', R¹, R², R³ and C are as defined above, with formation of phosphotriester groups, (d) blocking free primary 5'-OH groups, which have not been reacted in the reaction according to step (b), with permanent protective groups;

(e) eliminating the protective group R²;

(f) optionally repeating steps (a) to (e) to introduce further nucleoside phosphate or oligonucleoside phosphate units; and (g) cleaving the nucleoside carrier bond and optionally eliminating the protective groups present in the oligonucleoside phosphates, which process comprises using in step (a) as the phosphine derivative of the general formula III a compound in which R³ denotes a group of the formula VII

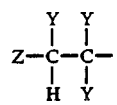

in which the groups Y, which can be identical or different, represent hydrogen, methyl, and/or ethyl and Z represents an electron-attracting group, where, in the phosphine derivative of the formula III, X is chlorine, bromine, CN or SCN and L is CN or SCN, a secondary amino radical of the formula (VIII)

—NR₂⁴ where the groups R⁴ are primary, secondary, or tertiary alkyl radicals having 1–10 carbon atoms, or together form a cycloalkyl radical having 5–7 carbon atoms, which can contain one or two nitrogen, oxygen, or sulfur atoms as hereoatoms, or are imidazole, triazole, tetrazole, 3-nitro-1,2,4-triazole, thiazole, pyrrole, benzotriazole, benzohydroxytriazole, imidazole substituted in the phenyl moiety, triazole substituted in the phenyl moiety, tetrazole substituted in the phenyl moiety, 3-nitro-1,2,4-triazole substituted in the phenyl moiety, thiazole substituted in the phenyl moiety, pyrrole substituted in the phenyl moiety, benzotriazole substituted in the phenyl moiety, or benzohydroxytrizole substituted in the phenyl moiety.

2. The process as claimed in claim 1, in which is used a phosphine derivative of the formula III in which X is chlorine or bromine, and L is a secondary amino radical of the formula (VIII)

$$-NR_2^4 \qquad (VIII)$$

where the groups $R^4$ are primary, secondary or tertiary alkyl radicals having 1-10 carbon atoms, or together form a cycloalkyl radical having 5-7 carbon atoms, which can contain one or two nitrogen, oxygen or sulfur atoms as heteroatoms, or are imidazole, triazole, tetrazole, 3-nitro-1,2,4-triazole, thiazole, pyrrole, benzotriazole, benzohydroxytriazole, imidazole substituted in the phenyl moiety, triazole substituted in the phenyl moiety, tetrazole substituted in the phenyl moiety, 3-nitro-1,2,4-triazole substituted in the phenyl moiety, thiazole substituted in the phenyl moiety, pyrrole substituted in the phenyl moiety, benzotriazole substituted in the phenyl moiety, or benzohydroxytrizole substituted in the phenyl moiety.

3. The process as claimed in claim 1 or 2, in which is used a phosphine derivative of the formula (III) in which X is chlorine, L is an N,N-dimethylamino, -diethylamino or -diisopropylamino group or N-morpholino group, and $R^3$ is a β-cyanoethyl group.

4. A method of preparing oligonucleotides of the general formula:

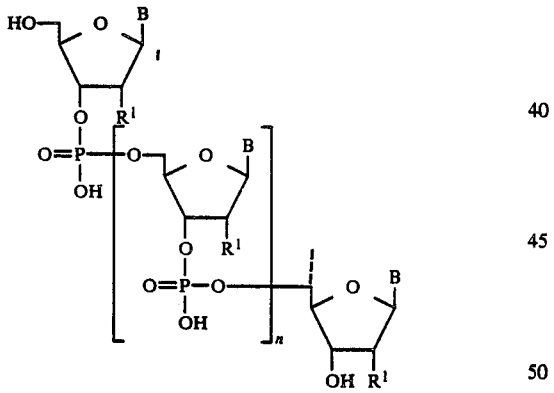

wherein B is a nucleoside base, $R^1$ is hydrogen, hydroxyl or hydroxyl which is protected by removable nucleoside protective groups, and n denotes an integer from 1 to 200, comprising the steps of:

(a) reacting a nucleotide phosphite represented by the formula:

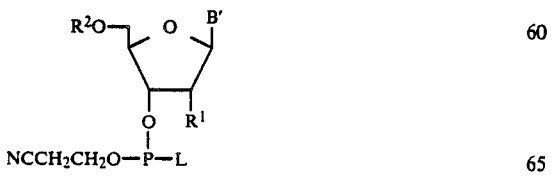

wherein B' is a nucleoside base B protected by a base protective group which can be eliminated, $R^1$ is as defined above, $R^2$ is 4,4' dimethoxytrityl or 4,4',4" trimethoxytrityl; and L is N,N-dimethylamino, N,N-diethylamino, N,N-diisopropylamino, or N-morpholino, with a nucleoside bound to a polymeric carrier, of the general formula:

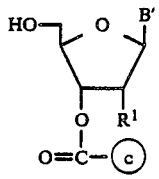

wherein B' and $R^1$ are as defined above and C represents the polymeric carrier, to produce a carrier bound nucleoside-nucleotide of the formula:

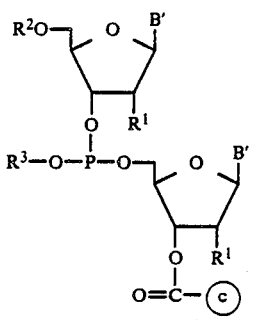

wherein B', $R^1$, $R^2$, $R^3$ and C are as defined above;

(b) oxidizing the carrier bound nucleoside-nucleotide;

(c) blocking free primary 5'-OH groups, which have not been reacted in the reaction of step (a), with permanent protective groups;

(d) eliminating the protecting group $R^2$;

(f) repeating steps (a) to (d) to introduce further nucleoside phosphate units; and (g) cleaving the nucleoside-carrier bond and optionally eliminating protective groups present in the oligonucleoside phosphates.

5. A method of synthesizing oligonucleotides, comprising the steps of:

(a) coupling a nucleoside β-cyanoethyl-protected phosphoramidite to a carrier-bound nucleoside to produce a carrier bound nucleoside-nucleotide having a phosphite triester linkage;

(b) oxidizing the phosphite triester to form a phosphate triester;

(c) optionally coupling additional nucleoside β-cyanoethyl-protected phosphoramidites to the carrier bound nucleoside-nucleotide and, after each coupling step, oxidizing the resulting phosphite triester to form a phosphate triester, to form a carrier bound polynucleotide;

(d) removing the β-cyanoethyl protecting groups; and (e) removing the polynucleotide from the carrier.

6. A method of claim 5, wherein the nucleoside β-cyanoethyl phosphoramidite is a nucleoside β-cyanoethyl N,N-dimethylphosphoramidite, N,N-diethylphosphoramidite, N,N-dipropylphosphoramidite or N,N-morpholino phosphoramidite.

7. A method of claim 6, wherein the carrier is controlled pore glass.

8. A method of claim 7, wherein the β-cyanoethyl protecting group is removed with simultaneous removal of the polynucleotide from the carrier, by concentrated aqueous ammonia.

9. In a method of polynucleotide synthesis, comprising sequentially coupling nucleotide phosphoramidites to produce a polynucleotide, wherein the phosphorus atoms of the nucleotide phosphoramidites are protected by methyl groups, the improvement wherein the phosphorus protecting group are cyanoethyl groups.

10. A method of synthesizing oligonucleotides, comprising the steps of:
   a. coupling a nucleoside β-cyanoethyl-protected phosphoramidite to a nucleoside, the nucleoside being bound to a polymeric carrier via an ester bond to produce a carrier-bound nucleoside-nucleotide having a phosphite triester linkage;
   b. oxidizing the phosphite triester to form a phosphate triester linkage;
   c. sequentially coupling additional nucleoside β-cyanoethyl protected phosphoramidite to the carrier-bound nucleoside-nucleotide, and after each coupling step, oxidizing the resulting phosphite triester linkage to a phosphate triester to produce a carrier-bound polynucleotide;
   d. treating the carrier bound polynucleotide with concentrated ammonia to remove the β-cyanoethyl phosphate protecting group and hydrolyzing the ester bond to the carrier to remove the polynucleotide from the carrier.

11. A method of claim 10, wherein the nucleoside β-cyanoethyl phosphoramidite is a nucleoside β-cyanoethyl N,N-dimethylphosphoramidite, N,N-diethylphosphoramidite; N,N-dispropylphosphoramidite or N,N-morpholino phosphoramidite.

12. A method of claim 10, wherein the carrier is controlled pore glass.

13. A protected nucleotide having the formula:

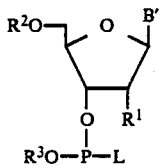

where,
B' is a nucleoside base protected by a base protective group which can be eliminated;
$R^1$ is H, OH, or a hydroxyl group which is protected by a removable nucleoside protective group;
$R^2$ is a removable protective group;
$R^3$ is

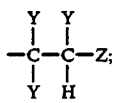

L is CN, SCN, or $NR_2^4$;
$R^4$ is a primary, secondary or tertiary alkyl radical having 1-10 carbon atoms, or $R_2^4$ is a cyloalkyl radical having 5-7 carbon atoms or a cycloalkyl radical having 5-7 atoms comprising atoms and one or two nitrogen, oxygen or sulfur atoms as heteroatoms;

Y is H, $CH_3$, or $CH_2CH_3$; and Z is a halgen, CN, $NO_2$, phenyl substituted in the o, o' or p positions with a halogen, CN or $NO_2$ radical, phenylthio, phenylsulfoxy, or phenylsulfonyl, where the phenyl radicals, may be substituted in the o, o' or p positions with a halgen, CN or $NO_2$ radical, or where the group

may be replaced by $CF_3$, $CCl_3$, or $CBr_3$.

14. A protected nucleotide as in claim 13, wherein Z is CN.

15. A protected nucleotide as in claim 14, wherein $R_3$ is $CH_2$—$CH_2$—CN.

16. A protected nucleotide as in claim 13, wherein $R_2$ is 4,4'-dimethoxytrityl or 4,4''-trimethoxytrityl.

17. A protected nucleotide having the formula:

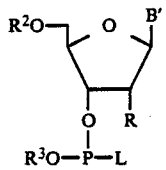

where,
$R^1$ is H, OH, or a hydroxyl group which is protected by a removable nucleoside protective group;
$R^2$ is 4,4'-dimethoxytrityl or 4,4',4''-trimethoxytrityl;
B' is a nucleoside base protected by a base protective group which can be eliminated
$R^3$ is $CH_2$—$CH_2$—CN; and
L is N,N-dimethylamino, N,N-diethylamino, N,N-diisopropylamino or N-morpholino.

18. A protected nucleotide having the formula:

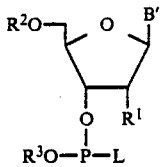

where,
$R^1$ is H, OH, or a hydroxyl group which is protected by a protective group selected from the group consisting of trityl groups, acyl groups and silyl ether groups;
$R^2$ is 4,4'-dimethoxytrityl or 4,4',4''-trimethoxytrityl;
B' is a nucleoside base selected from the group consisting of adenine, guanine, cytosine, thymine, uracil and analogs thereof which are protected by acyl groups or Schiff bases;
$R^3$ is $CH_2$—$CH_2$—CN; and
L is N,N-dimethylamino, N,N-diethylamino, N,N-diisopropylamino, or N-morpholino.

19. A protected nucleotide of claim 18, wherein $R_1$ is H and B' is adenine, guanine, cytosine, thymine or uracil wherein the adenine or guanine is protected by a benzoyl group and the guanine is protected by an isobutyl group.

* * * * *